United States Patent
West et al.

(10) Patent No.: US 7,410,283 B2
(45) Date of Patent: Aug. 12, 2008

(54) DENTAL LIGHT GUIDE

(75) Inventors: John West, Arroyo Grande, CA (US); Scott Ganaja, San Luis Obispo, CA (US)

(73) Assignee: Den-Mat Holdings LLC, Santa Maria, CA (US)

( * ) Notice: Subject to any disclaimer, the term of this patent is extended or adjusted under 35 U.S.C. 154(b) by 162 days.

(21) Appl. No.: 10/715,540

(22) Filed: Nov. 19, 2003

(65) Prior Publication Data

US 2004/0141336 A1    Jul. 22, 2004

Related U.S. Application Data

(60) Provisional application No. 60/427,210, filed on Nov. 19, 2002.

(51) Int. Cl.
    *A61B 1/07*    (2006.01)
    *F21V 13/12*   (2006.01)
    *A61C 3/00*    (2006.01)

(52) U.S. Cl. ........................ 362/573; 362/327; 362/555; 362/577; 433/29

(58) Field of Classification Search .................. 362/555, 362/572, 573, 581, 577, 578, 327, 551; 385/902, 385/33–35, 93; 433/29, 30
    See application file for complete search history.

(56) References Cited

U.S. PATENT DOCUMENTS

| | | | | |
|---|---|---|---|---|
| 2,362,175 A | * | 11/1944 | Swanson | 385/147 |
| 4,730,909 A | * | 3/1988 | Takahashi | 385/117 |
| 4,767,172 A | * | 8/1988 | Nichols et al. | 385/146 |
| 4,883,333 A | * | 11/1989 | Yanez | 385/33 |
| 5,290,169 A | * | 3/1994 | Friedman et al. | 433/29 |
| 5,420,768 A | | 5/1995 | Kennedy | |
| 5,634,711 A | | 6/1997 | Kennedy et al. | |
| 5,803,729 A | * | 9/1998 | Tsimerman | 433/29 |
| 6,181,369 B1 | * | 1/2001 | Ooshima et al. | 433/29 |
| 6,200,134 B1 | * | 3/2001 | Kovac et al. | 433/29 |
| 6,406,293 B1 | * | 6/2002 | Burstein | 433/29 |
| 6,527,411 B1 | * | 3/2003 | Sayers | 362/555 |
| 6,857,873 B2 | * | 2/2005 | Bianchetti et al. | 433/29 |
| 7,029,277 B2 | * | 4/2006 | Gofman et al. | 433/29 |
| 2001/0024777 A1 | * | 9/2001 | Azar et al. | 433/29 |
| 2003/0081430 A1 | * | 5/2003 | Becker | 433/29 |
| 2004/0029069 A1 | * | 2/2004 | Gill et al. | 433/29 |

OTHER PUBLICATIONS

European Search Report dated Jan. 18, 2008 (Four (4) pages).

* cited by examiner

*Primary Examiner*—Alan Cariaso
(74) *Attorney, Agent, or Firm*—John W. Ryan; Crowell & Moring LLP

(57) ABSTRACT

The present invention is a device that attaches to a light source to transmit and distribute light energy to the surface or internal chamber of a tooth for the purpose of photo-initiation of light curing resins and dental tooth whitening. More particularly, the invention may be used with a single or multiple Light Emitting Diode(s) to more efficiently collect and transmit the light energy emitted by the LED(s) resulting in increased total energy, uniform illumination, and collimation of the light energy delivered to the tooth.

7 Claims, 9 Drawing Sheets

PRIOR ART REFERENCE: OPTILUX 501

DENTAL LIGHT GUIDE

REFERENCE TO RELATED APPLICATION

This application claims the benefit of U.S. Provisional Application No. 60/427,210, filed Nov. 19, 2002, which is hereby incorporated by reference.

FIELD OF INVENTION

This invention relates to light guides and light-curing apparatus for producing a beam of light for photo-initiating a light curing dental composition. In particular, the present invention is a device that attaches to a Light Emitting Diode (LED) light source to transmit and distribute light energy to the surface or internal chamber of a tooth for the purpose of photo-initiation of light curing resins and dental tooth whitening.

BACKGROUND

Dentistry relies on light curing resins as sealants, adhesives, and as filler material for filling dental cavities. Light curing material is cured by exposure to radiant energy in spectral range tailored to the composition of the material. A light-curing unit containing a reflector lamp is used to irradiate the light curing material by directing light from the reflector lamp through a light guide positioned with its distal end adjacent to the light curing material to be cured. The light guide functions to channel the light to the material at the site of the dental restoration.

The physics of the transmission of light through a light conductor is well known. Practical factors and physical limitations of both doctor and patient often dictate the design of the light guides and light-curing units used in modern dentistry. The need for accessibility and maneuverability within the oral cavity of a patient requires the light guide to have a curved end section. Aside from these practical considerations attention must also be given to maximizing the transmission of light from the light source.

Conventional light guides typically comprise a solid conductor of either glass or plastic, or is composed of a fiber optic conductor consisting of multiple strands of glass fiber held together as a flexible bundle or fused into a solid rod of individual fibers. Conventional light guides are not as efficient as the instantly disclosed light guide as they typically produce high angle light that results in loss of light energy due to multiple reflections and the escape of light from the apparatus.

Light sources used for the purpose of photo-initiation of light curing resins and dental tooth whitening fall into two major categories. Light sources such as tungsten halogen, metal halide, and xenon all produce white light that is filtered to transmit only visible light within the general spectral range of 380-520 nanometers. Light sources such as laser and light emitting diode produce visible light which is closely matched to the photo-initiators used in light curing resins and activators found in dental tooth whitening formulations.

Light sources such as tungsten halogen, metal halide, and xenon are not very efficient at producing light energy within the spectral range useful for dental photo-polymerization and tooth whitening. The energy produced by these light sources in the form of ultraviolet and infrared is not used in the dental application. Light sources such as laser and LED that produce visible blue light with spectral output closely matching the photo-initiators used in dental resins and the activators found in dental tooth whitening formulations are much more efficient and produce less heat in the form of infrared wavelengths. Light emitting diodes last for thousands of hours with no degradation in light output eliminating the need to change lamps.

Prior use of Light Emitting Diodes for dental light sources relied on multiple LED's placed in arrays to generate enough power to be practical for dental curing. This is expensive and also increases the size of the device. Recent advancements in LED semiconductor technology have resulted in the introduction of a single blue LED that emits radiometric power levels sufficient to allow the rapid photo-polymerization of light curing resins and for use in dental tooth whitening. It is recognized that continued advancements in LED semiconductor technology will result in the use of different semiconductor substrate materials to alter the color spectra as well as increase radiometric power for single LED devices.

The domed lens cover used as part of the construction of these mass-produced LED's is designed so that light is visible from 360 degrees around the device. This is because the typical application for these devices are indicator lights such as traffic signal lights, automotive brake and signal lights, and signage. The present invention redirects the light energy emitted from the LED and focuses it toward the distal end of the invention in an efficient manner resulting in higher energy levels than possible with a traditional external reflector.

SUMMARY OF THE INVENTION

The present invention provides a dental light guide comprising an entrance area, a lens, at least one reflector, a light pipe and an exit area.

The present invention also provides a dental light guide comprising an entrance area, a lens, at least one reflector, a light pipe and an exit area and wherein the dental light guide is comprised of injection molded acrylic, glass or plastic.

The present invention also provides multi-piece dental light guide comprising an entrance area, at least one reflector, and lens all functionally attached to an image conduit by a metal sleeve.

Additionally, the present invention provides a multi-piece dental light guide comprising an entrance area, at least one reflector, and lens all functionally attached to an image conduit by a metal sleeve and wherein the entrance area, at least one reflector and lens are molded in a single glass part.

The present invention further provides an apparatus for the purpose of providing light for the photo-initiation of light curing resins, comprising a light source and a light guide for transmitting reflected light from said light source as a concentrated, high-intensity beam, said light comprising an entrance area, a lens, at least one reflector, a light pipe and an exit area.

The present invention further provides an apparatus for the purpose of providing light for the photo-initiation of light curing resins, comprising a light source and a light guide for transmitting reflected light from said light source, said light comprising an entrance area, a lens, at least one reflector, a light pipe and an exit area wherein the light source is LED, tungsten halogen, metal halide, or xenon.

DETAILED DESCRIPTION OF THE INVENTION

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

The instantly disclosed invention is the current industry standard light curing tip for dental composites. It was originally based on receiving light from a halogen, xenon, or other similar light source. LED light sources have different requirements, however. First, the light emitter is small. This allows the proximal end of the light guide to be very close to the emitter and even envelop the source. Secondly, LED's emit very little heat forward (although they do emit heat rearwards). This allows the use of transparent plastics for construction of the light guide as well as single or multiple glass elements. Molded plastics and glass allow for much more complex shapes giving more optical design freedom. Finally, although LED's are efficient they currently do not provide as much total light as traditional light sources. This requires that the light guide be very efficient. Current light sources can use less efficient tips because they have surplus power.

The instant invention is designed to work with single or multiple LED emitters with or without domed lens covers to control beam geometry. Light sources used for dental curing and whitening procedures traditionally delivered light energy to the tooth through a rigid light guide commonly known as fused glass or image conduit constructed of thousands of individual fiber optic strands. Single plastic rods and glass-clad rods have also been used. These rigid light guides connect to the light source and light enters into the proximal end and is delivered at the distal end. The light travels through the rigid light guide and exits the distal end at approximately the same angle as it entered. More recently, LED light sources have been introduced where the emitter, covered by a lens cap, is placed in close proximity to the tooth. An external reflector is used to focus the light to the target area in front of the light source.

Figure 1:
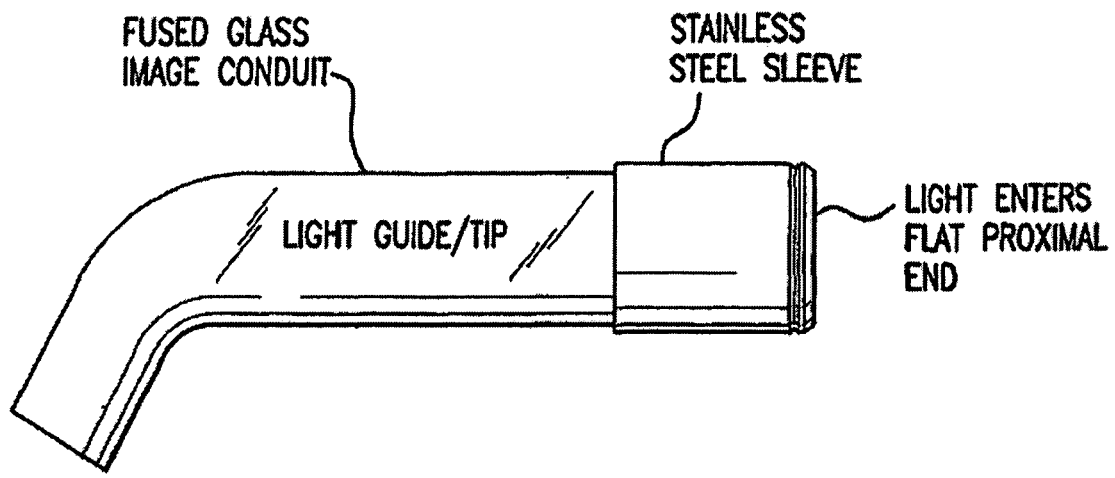
FIG. 1 illustrates a conventional light guide.
Figure 2:
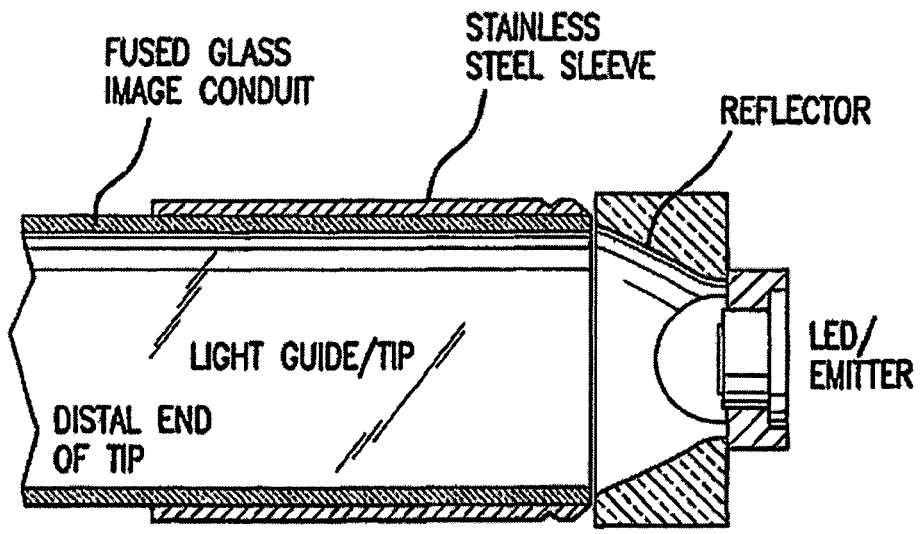
FIG. 2 illustrates another conventional light guide.
Figure 3:
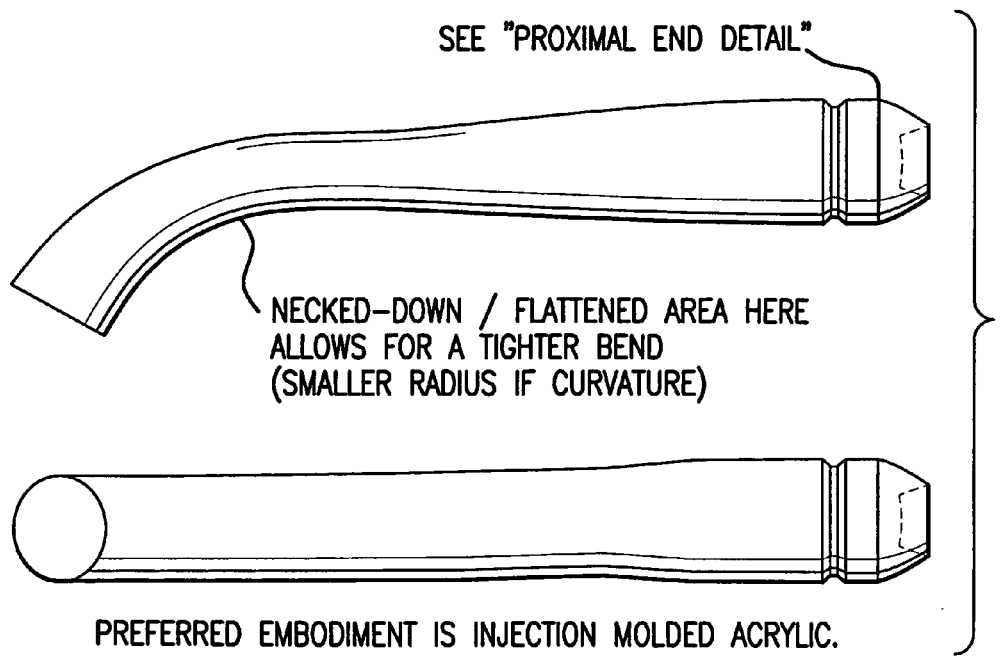
FIG. 3 illustrates an embodiment of the instant invention.
Figure 4:
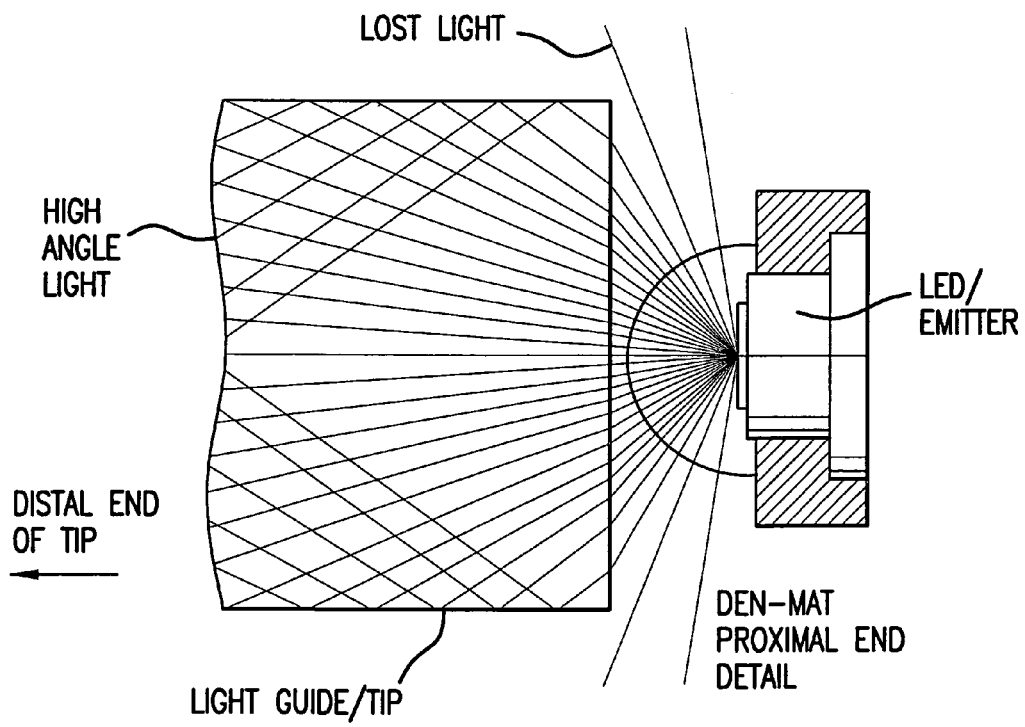
FIG. 4 illustrates the inefficiencies of flat-ended light guides.
Figure 5:
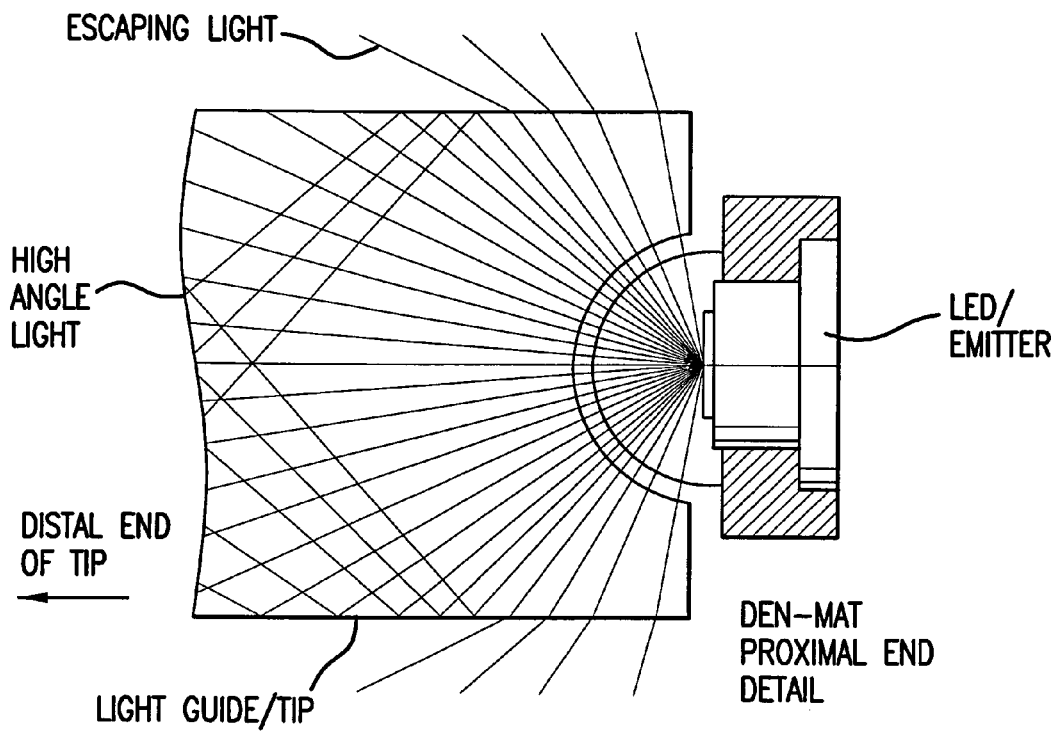
FIG. 5 illustrates the inefficiencies of light guides without total internal reflection.
Figure 6:
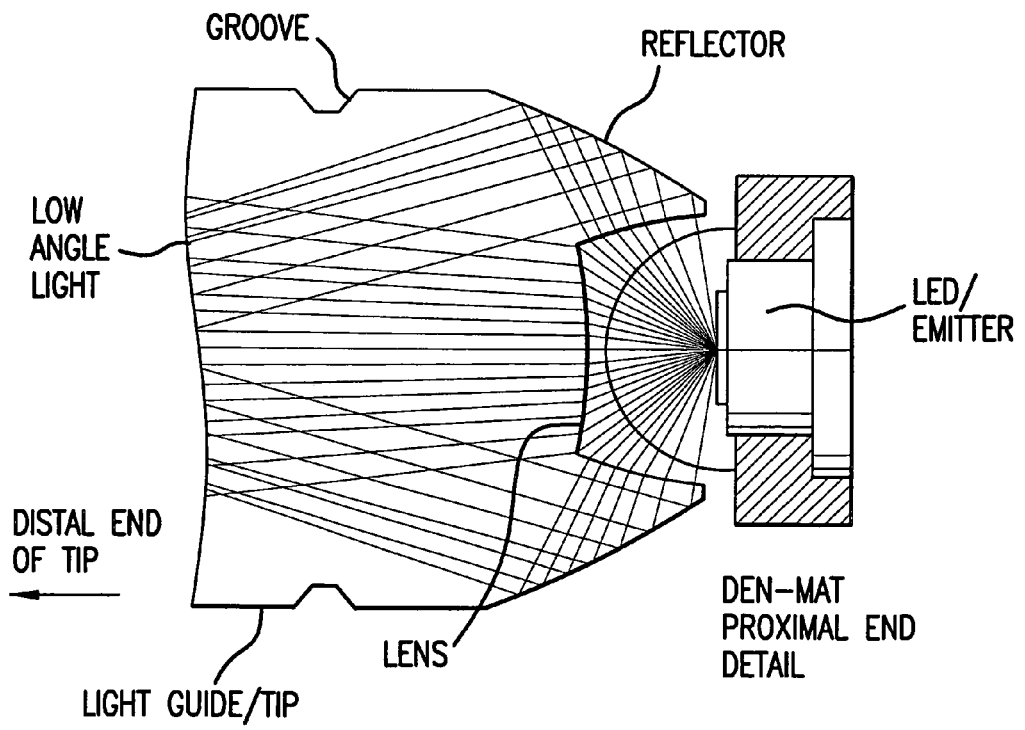
FIG. 6 illustrates the efficiency of an embodiment of the instant invention.

Most first-generation LED curing devices use flat proximal end tips made from fused glass (see FIG. 1). A metallic or metal-coated plastic reflector is used to reflect light forward into the light guide (see FIG. 2). Metal reflectors are typically 60-90% efficient compared to acrylic total internal reflection type reflectors which can be over 96% efficient.

Figure 7:
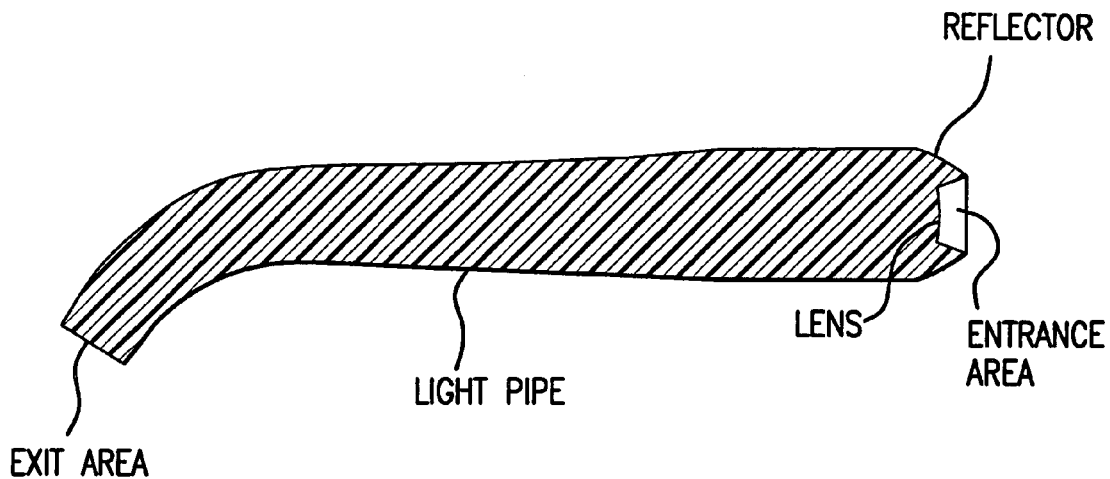
FIG. 7 illustrates a further embodiment of the instant invention.

One embodiment of the instant invention consists of five basic features: the entrance area, the reflector, the lens, the light pipe, and the exit area. In a one-piece molded tip, all five features are molded together. See FIG. 7.

Figure 8:
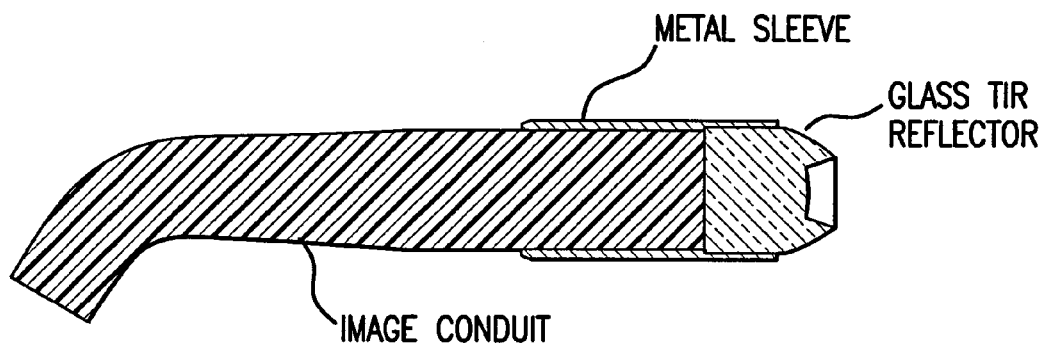
FIG. 8 illustrates an additional embodiment of the instant invention.

An alternate embodiment involves the use of a multi-piece tip. In this particular embodiment the pieces are the TIR reflector, the sleeve, and the image conduit. See FIG. 8.

The first piece, the TIR reflector, comprises three features including the entrance area, the reflector, and the lens. These features are molded into a single glass part in the preferred embodiment. The geometry and function of these three features is the same as in the one-piece version.

The second piece is a metal sleeve that is used to connect the TIR reflector to the image conduit. An adhesive may be used to secure in the connection.

The third piece, the image conduit, provides a means to transmit the light from the TIR reflector to the exit area, similar in purpose to the light pipe portion of the molded one-piece tip. Image conduit is typically constructed of small glass rods (fiber optics) fused together to form a large bundle (conduit). Image conduit is more efficient at transmitting light around a bend than a simple light pipe. Because the conduit is designed to transmit an image, the pattern of light at its entrance is virtually the same as the light pattern at the exit. The light intensity at the exit area is higher and the light distribution is more uniform compared to a molded light pipe.

Figure 9:
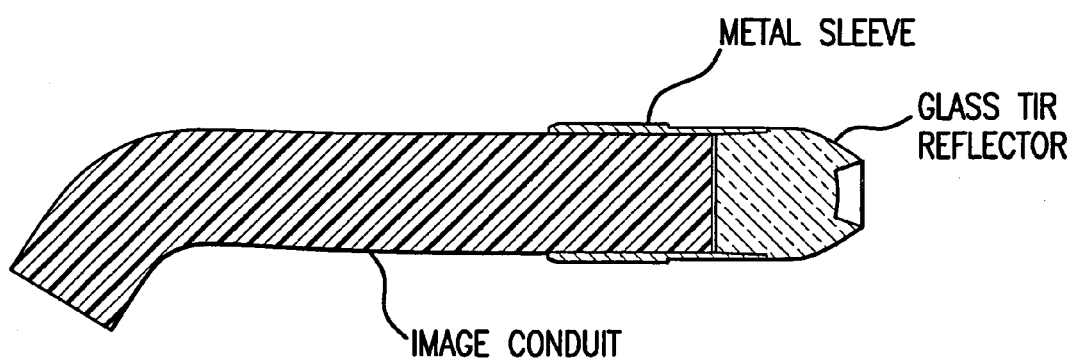
FIG. 9 illustrates another further embodiment of the instant invention.

Another alternate design involves the same features and parts as the above described three piece tip with slightly altered geometry. The larger reflector area allows more light to be directed into the image conduit. This version is more difficult to manufacture. See FIG. 9.

FIGS. 4-9 illustrate additional embodiments of the instant invention.

High angle light is light that forms a large angle to the axis of the light guide. High angle light is not as useful as low angle light for two reasons. First, high angle light hits the walls more frequently resulting in higher losses (light loses energy every time that it is reflected). Secondly, high angle light escapes out of the distal end at high angles, resulting in a wider pattern (cone of light). This results in a more rapid reduction of intensity the further away from the tip the measurement is taken. See FIG. 4.

LED enveloped by light guide. For reference only. More efficient. Light escapes around the sides of the light guide because it does not internally reflect (it refracts). No total internal reflection (TIR). Most of the light is high angle light. See FIG. 5.

Combination of LED enveloped by light guide, molded-in TIR reflector, and molded-in lens. This preferred embodiment is very efficient. Light is split into two paths. The outer light is directed onto the TIR reflector and reflects forward at a relatively low angle. The inner light rays are refracted into the tip at a lower angle than that of a flat tip. After designing this tip, a flashlight lens was discovered that uses acrylic molded-in TIR reflector and lens. Similar to the instant invention except that the instant invention focuses light into and through the tip compared to emitting light out into the air for illumination. The advantages over current tips is more efficient light transfer and much lower manufacturing cost. See FIG. 6.

The tip consists of five basic features. The entrance area, the reflector, the lens, the light pipe, and the exit area. In a one-piece molded tip, all five features are molded together. See FIG. 7.

The first alternate embodiment involves the use of a three-piece tip. The three pieces are the TIR reflector, the sleeve, and the image conduit. See FIG. 8.

The first piece, the TIR reflector, comprises three features including the entrance area, the reflector, and the lens. These features are molded into a single glass part in the preferred embodiment. The geometry and function of these three features is the same as in the one-piece version.

The second piece is metal sleeve that is used to connect the TIR reflector to the image conduit. Adhesive is also involved in the connection.

The third piece, the image conduit, provides a means to transmit the light from the TIR reflector to the exit area, similar in purpose to the light pipe portion of the molded one-piece tip. Image conduit is typically constructed of small glass rods (fiberoptics) fused together to form a large bundle (conduit). Image conduit is more efficient at transmitting light around a bend than a simple light pipe. Because the conduit is designed to transmit an image, the pattern of light at its entrance is virtually the same as the light pattern at the exit. The light intensity at the exit area is higher and the light distribution is more uniform compared to a molded light pipe.

A second alternate design involves the same features and parts with slightly altered geometry. The larger reflector area allows more light to be directed into the image conduit. This version is more difficult to manufacture. See FIG. 9. Both three-piece tip designs provide more light in a more uniform pattern, but are more expensive to manufacture compared to the one-piece version.

| Date | Time | Text | uWatt | uWatt/cm$^2$ | mW/cm2 | peak at | peak val | FWHM |
|---|---|---|---|---|---|---|---|---|
| | | Calibration Aug. 25, 2003 | 8437 | 600 | | 93.71 | 350.9 | |
| | | Allegro 8 mm Acrylic Aug. 25, 2003 | 624585 | 451 | | 20874.39 | 26.56 | |
| | | Allegro 8 mm Acrylic Aug. 25, 2003 | 627734 | 451 | | 21121.49 | 26.35 | |
| | | Allegro 407 TIR | 515152 | 451 | | 16968.6 | 26.92 | |
| | | SF No Filter 8.29 | 237807 | 468 | | 1382.95 | 318.51 | |
| | | optilux 501 8 mm turbo | 433665 | 476 | | 5654.4 | 85.75 | |
| | | sapphire 9 mm | 867759 | 468 | | 9827.2 | 107.6 | |
| | | sapphire 9 mm | 1098140 | 468 | | 12201.63 | 109.2 | |
| Nov. 13, 2003 | 12:19:04 PM | Allegro 0 mm Cosine | 209514 | 1753860 | 1754 | 438.69 | 67795.12 | 22.35 |
| Nov. 13, 2003 | 12:22:52 PM | Allegro 2 mm Cosine | 255267 | 2136860 | 2137 | 438.69 | 81915.93 | 22.61 |
| Nov. 13, 2003 | 12:24:11 PM | Allegro 4 mm Cosine | 211002 | 1766320 | 1766 | 438.69 | 68308.14 | 22.34 |
| Nov. 13, 2003 | 12:30:23 PM | Allegro 6 mm Cosine | 149187 | 1248860 | 1249 | 440.47 | 48042.42 | 22.39 |
| Nov. 13, 2003 | 12:40:00 PM | Allegro 8 mm Cosine | 86114 | 720866 | 721 | 440.47 | 28131.62 | 22.2 |
| Nov. 13, 2003 | 12:43:02 PM | Allegro 10 mm Cosine | 62618 | 524180 | 524 | 440.47 | 20774.24 | 21.95 |
| Nov. 13, 2003 | 2:56:22 PM | LEDemetron 0 mm Cosine (8 mm tip) | 188719 | 1579780 | 1580 | 453.25 | 55174.59 | 24.86 |
| Nov. 13, 2003 | 4:17:58 PM | LEDemetron 2 mm Cosine (8 mm tip) | 176191 | 1474910 | 1475 | 453.25 | 51724.84 | 24.67 |
| Nov. 13, 2003 | 4:29:59 PM | LEDemetron 4 mm Cosine (8 mm tip) | 110872 | 928118 | 928 | 454.32 | 32969.58 | 24.32 |
| Nov. 13, 2003 | 4:30:41 PM | LEDemetron 6 mm Cosine (8 mm tip) | 66741 | 558694 | 559 | 454.32 | 20324.88 | 24.09 |
| Nov. 14, 2003 | 10:19:05 AM | LEDemetron 8 mm Cosine(8 mm tip) | 36237 | 303341 | 303 | 453.25 | 11332.93 | 23.94 |
| Nov. 14, 2003 | 10:26:36 AM | LEDemetron 10 mm Cosine (8 mm tip) | 18396 | 153996 | 154 | 454.32 | 5929.78 | 22.43 |
| Nov. 13, 2003 | 4:49:17 PM | LEDemetron 0 mm Cosine #2 (8 mm tip) | 190676 | 1596160 | 1596 | 453.25 | 54515.59 | 25.33 |
| Nov. 13, 2003 | 4:58:57 PM | LEDemetron 2 mm Cosine #2 (8 mm tip) | 190844 | 1597570 | 1598 | 453.25 | 56165.05 | 24.69 |
| Nov. 13, 2003 | 5:23:38 PM | LEDemetron 4 mm Cosine #2 (8 mm tip) | 115963 | 970733 | 971 | 454.32 | 34097 | 24.6 |
| Nov. 14, 2003 | 10:13:28 AM | LEDemetron 6 mm Cosine (8 mm tip) | 66824 | 559390 | 559 | 453.25 | 20487.79 | 23.78 |
| Nov. 14, 2003 | 10:19:05 AM | LEDemetron 8 mm Cosine #2 (8 mm tip) | 36237 | 303341 | 303 | 453.25 | 11332.93 | 23.94 |
| Nov. 14, 2003 | 10:28:11 AM | LEDemetron 10 mm Cosine #2 (8 mm tip) | 17947 | 150233 | 150 | 454.32 | 5864.72 | 22.47 |
| Nov. 14, 2003 | 11:21:38 AM | Flashlite 1001 0 mm Cosine | 81330 | 680821 | 681 | 465.28 | 24134.9 | 24.4 |
| Nov. 14, 2003 | 11:25:16 AM | Flashlite 1001 2 mm Cosine | 66112 | 553427 | 553 | 465.28 | 19743.74 | 24.45 |
| Nov. 14, 2003 | 11:28:49 AM | Flashlite 1001 4 mm Cosine | 42305 | 354141 | 354 | 465.28 | 12978.1 | 24.06 |
| Nov. 14, 2003 | 11:32:42 AM | Flashlite 1001 6 mm Cosine | 32476 | 271855 | 272 | 465.28 | 10022.17 | 24.17 |
| Nov. 14, 2003 | 11:36:50 AM | Flashlite 1001 8 mm Cosine | 22234 | 186118 | 186 | 465.28 | 7090.57 | 23.71 |
| Nov. 14, 2003 | 11:41:18 AM | Flashlite 1001 10 mm Cosine | 17305 | 144863 | 145 | 465.28 | 5600.43 | 23.39 |
| Nov. 14, 2003 | 4:02:25 PM | Allegro 0 mm Cosine | 168710 | 1412280 | 1412 | 443.67 | 52576.88 | 23.53 |
| Nov. 14, 2003 | 3:40:47 PM | Allegro 2 mm Cosine | 224282 | 1877480 | 1877 | 443.67 | 69844.88 | 23.35 |
| Nov. 14, 2003 | 3:44:23 PM | Allegro 4 mm Cosine | 184282 | 1542640 | 1543 | 443.67 | 57557.02 | 23.36 |
| Nov. 14, 2003 | 3:50:22 PM | Allegro 6 mm Cosine | 132681 | 1110680 | 1111 | 443.67 | 41738.62 | 23.21 |
| Nov. 14, 2003 | 3:55:58 PM | Allegro 8 mm Cosine | 86001 | 719919 | 720 | 444.02 | 27388.65 | 23.03 |
| Nov. 14, 2003 | 3:59:20 PM | Allegro 10 mm Cosine | 59328 | 496637 | 497 | 444.02 | 19171.72 | 22.91 |
| | | 0 mm | | 1412 | 1580 | 681 | | |
| | | 2 mm | | 1877 | 1475 | 553 | | |
| | | 4 mm | | 1543 | 928 | 354 | | |
| | | 6 mm | | 1111 | 559 | 272 | | |
| | | 8 mm | | 720 | 303 | 186 | | |
| | | 10 mm | | 497 | 154 | 145 | | |

Figure 10:
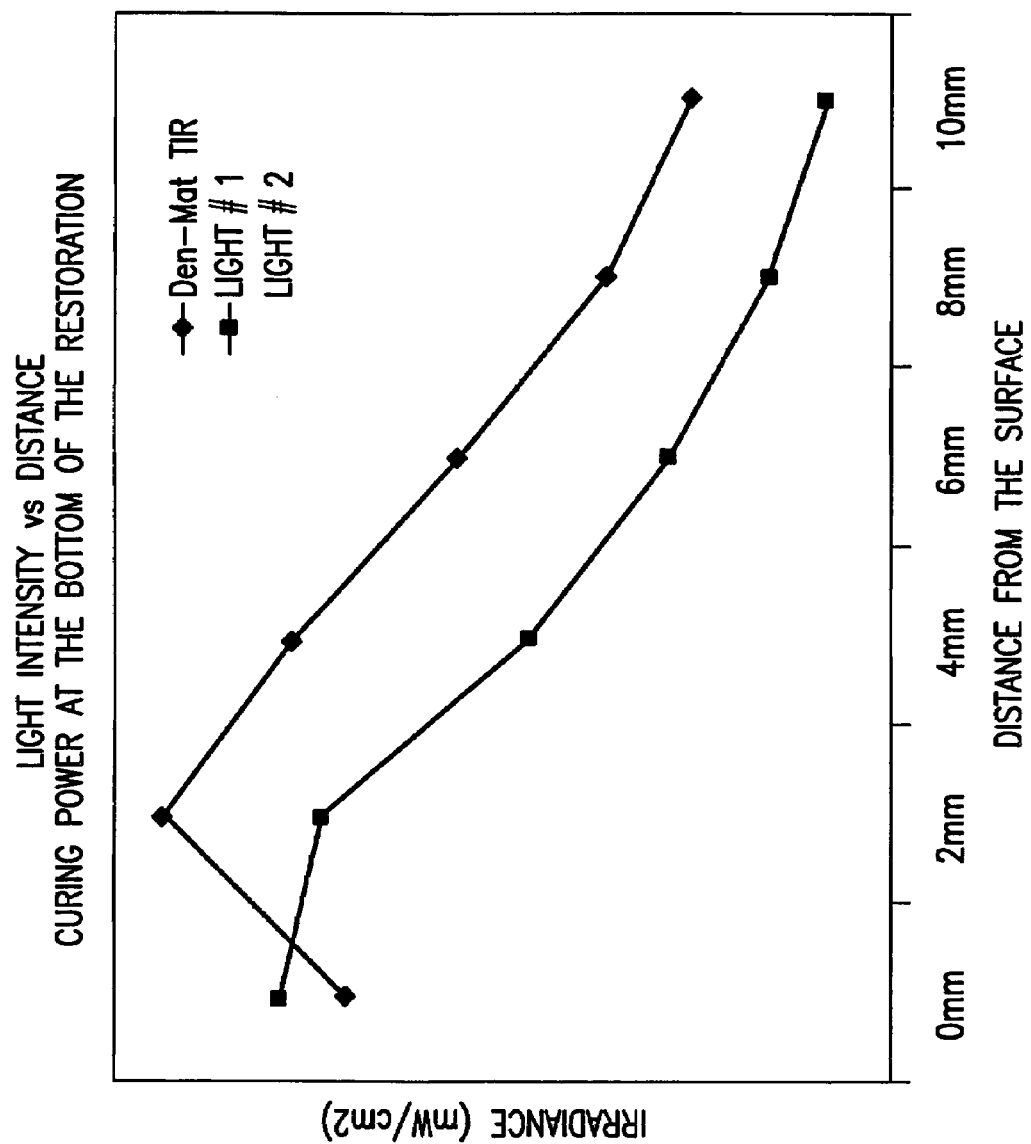
FIG. 10 is a chart illustrating that light intensity (mW/cm2) disperses rapidly with distance from these light sources.

See FIG. 10.

Each of the above described multi-piece tip designs provide more light in a more uniform pattern.

EXAMPLE 1

It has been demonstrated that light intensity (mW/cm2) disperses rapidly with distance from these light sources. The exit angle of the light as it leaves the light source contributes greatly to this. As the beam spread increases the light looses intensity rapidly. This is clinically significant to the practicing dentist and their patients. The bottom floor of a typical preparation may be a minimum of 2 mm deep or more. If the light intensity is too low at the bottom of the filling the composite material may not receive enough energy to adequately cure. Even if the composite is placed directly on the surface of the tooth the dentist holds the distal end of the light guide approximately 2 mm away to keep the composite from adhering to it. The clinical advantage of the present invention is that the light intensity mW/cm2) increases at 2 mm away from the surface and stays higher as distance increases. This facilitates complete curing of the composite. The results of this experiment can be seen in FIG. 10.

EXAMPLE 2

Figure 11A:
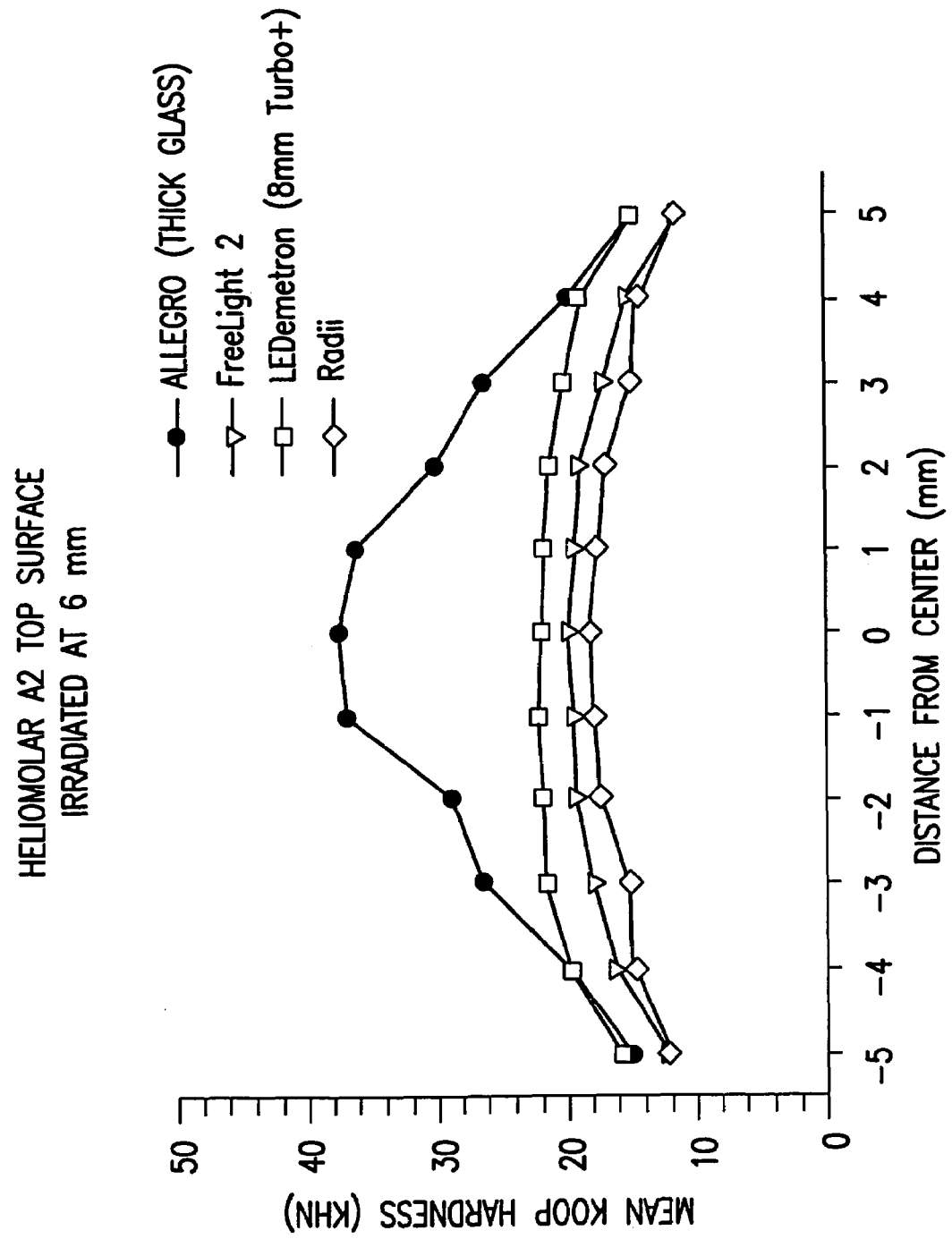
FIG. 11 demonstrates the effect of light collimation with an embodiment of the instant invention on a composite (Heliomolar) that is hard to cure.
Figure 11B:
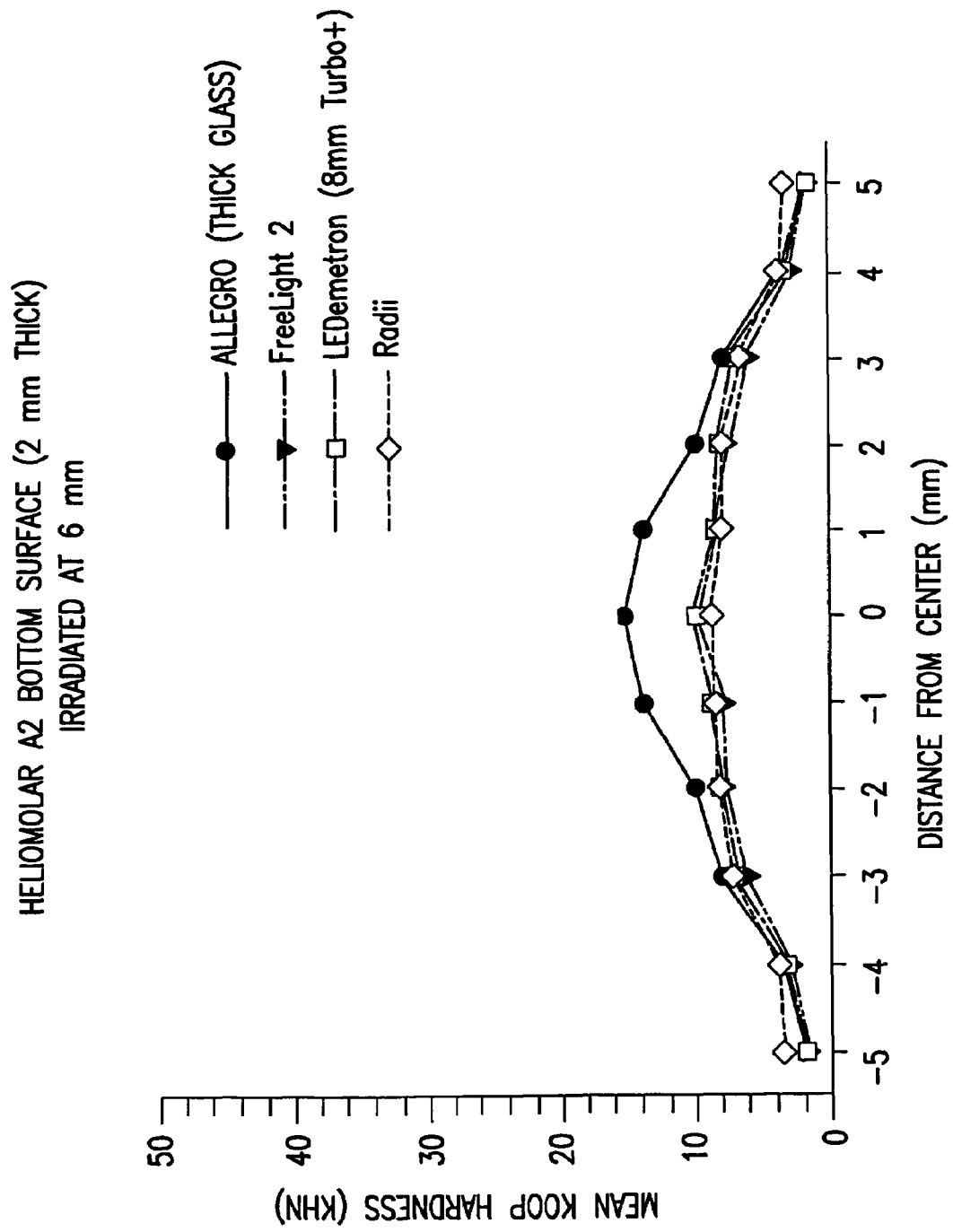
Figure 12A:
FIG. 12 is a photograph illustrating a curing distance of 6 mm.
Figure 12B:
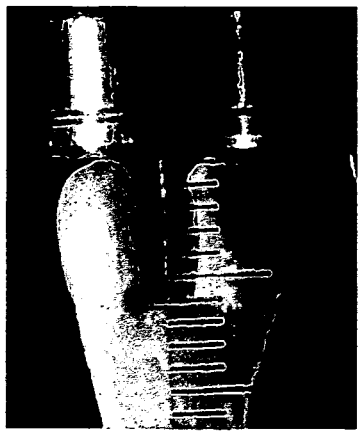
Figure 12C:
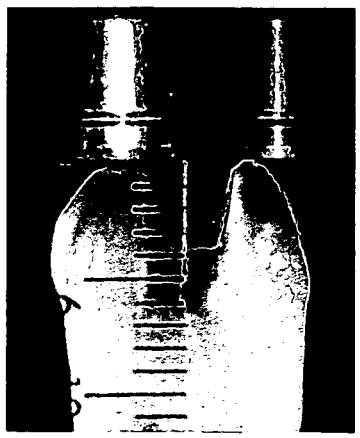

The effect of light collimation with an embodiment of the instant invention (identified in FIG. 11 as "Allegro") on a composite (Heliomolar) that is hard to cure is shown in the FIG. 11. FIG. 11 also compares the embodiment of the instant invention to the other 3 best LED-curing lights on the market. The instant invention is clearly superior. The composite was cured at a distance of 6 mm. See FIG. 12. The vertical axis shows the hardness value. Knoop Hardness (KHN) is considered, by academics, the most accurate test of composite hardness. Greater hardness means the composite has polymerized to a greater degree. This improves strength and wear and decreases the likelihood of sensitivity. The bottom of the sample is actually 8 mm away from the distal end of the tip.

Figure 13A:
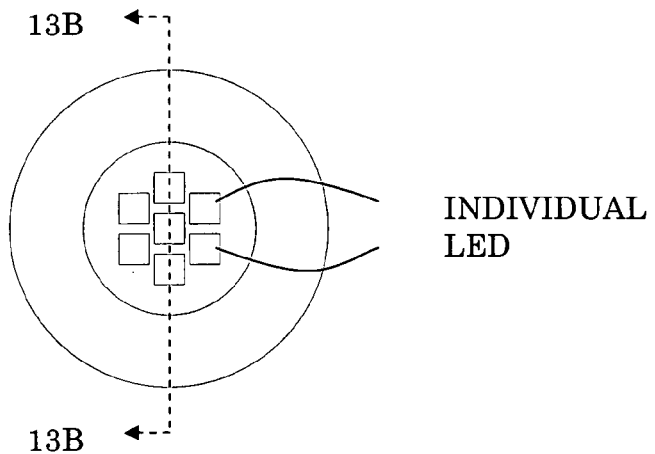
FIG. 13A illustrates a top view of a multiple LED embodiment of the present invention.
Figure 13B:
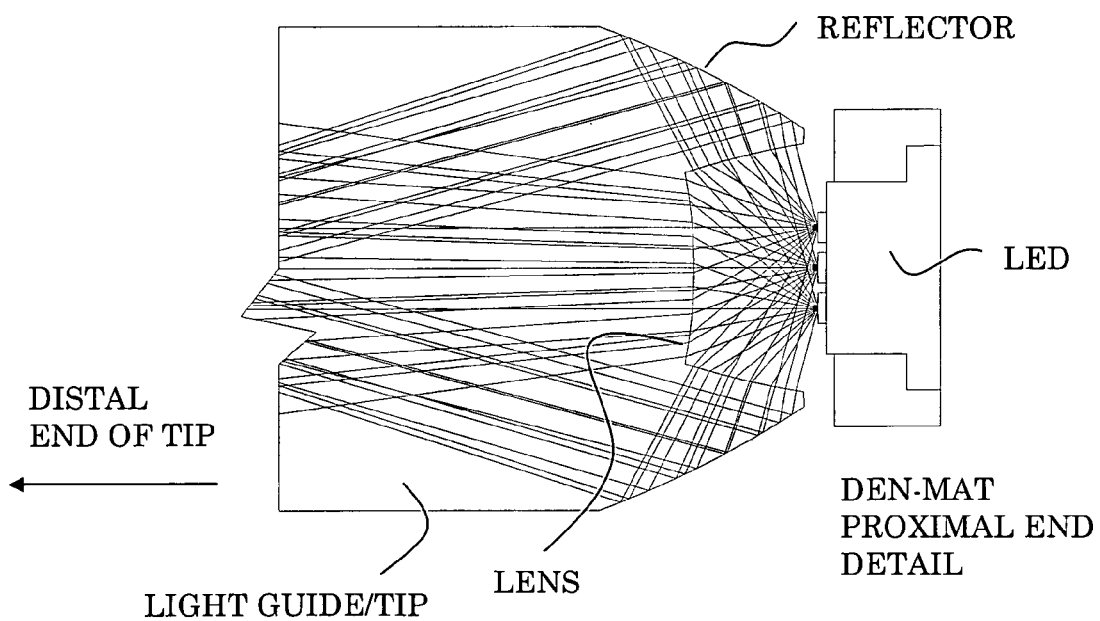
FIG. 13B illustrates a cross-sectional view of a multiple LED embodiment of the present invention.

FIG. 13A illustrates a top view of a multiple LED embodiment of the present invention. The cross-sectional view is shown in FIG. 13B. In this embodiment, the light source comprises an array of individual LED each formed without a domed lens.

The foregoing detailed description has been given for clearness of understanding only and no unnecessary limitations should be understood there from as modifications will be obvious to skilled in the art.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed:

1. A light guide for use in a dental curing device, said light guide comprising an entrance area, a lens, at least one reflector, and a light pipe having an exit area wherein the lens, at least one reflector, and light pipe are constructed of a single continuous homogeneous material and wherein said light pipe is curved such that the exit area of the light pipe is out of line with the entrance area of said light guide and said exit area is sized to be placed inside a patient's mouth such that light is projected onto a single tooth and wherein the light guide consists of a single material selected from the group consisting of acrylic, plastic and glass.

2. A multi-piece light guide for use in a dental curing device, said light guide comprising an entrance area, at least one reflector, and lens all functionally attached to an image conduit by a metal sleeve wherein the lens and at least one reflector are constructed of a single continuous homogeneous material and wherein the image conduit comprises a proximal end and a distal end and wherein the distal end is sized to be placed inside a patient's mouth such that light is projected onto a single tooth wherein the entrance area, at least one reflector and lens are in a single glass part.

3. The multi-purpose light guide of claim 2, wherein the image conduit is a fused fiber optic image conduit.

4. The multi-piece light guide of claim 2, wherein the image conduit is curved.

5. The multi-purpose light guide of claim 2, wherein the light source is LED, tungsten, halogen, metal halide or xenon.

6. The multi-purpose light guide of claim 2, wherein the light source is multiple LEDs.

7. The multi-purpose light guide of claim 2, wherein the sleeve is connected to the image conduit with adhesive.

* * * * *